United States Patent [19]
Bond et al.

[11] Patent Number: 6,051,186
[45] Date of Patent: Apr. 18, 2000

[54] CONTAINER AND DEVICES TO ASSURE STERILIZATION OF SURFACES AND DEVICES BY ELECTRIC FIELD AND STERILIZING MEDIA

[76] Inventors: James D. Bond; Bruce Sangster, both of 3857 Birch St., Suite 556, Newport Beach, Calif. 92660

[21] Appl. No.: 09/114,667
[22] Filed: Jul. 13, 1998
[51] Int. Cl.$^7$ .................................. A61L 2/08; A61L 2/18
[52] U.S. Cl. ............................ 422/22; 422/300; 220/339; 220/344; 206/370
[58] Field of Search ...................... 422/22, 300; 220/253, 220/255, 256, 339, 344; 206/370

[56] References Cited

U.S. PATENT DOCUMENTS

| | | | |
|---|---|---|---|
| 4,643,303 | 2/1987 | Arp et al. | 422/300 X |
| 4,919,888 | 4/1990 | Spence | 422/300 X |

*Primary Examiner*—Elizabeth McKane

[57] ABSTRACT

A container system is disclosed which effects sterilization of devices and objects by electric field and sterilizing media in substantially less time than that required by other sterilizing methods. The container system produces a totally enclosed and secure container.

2 Claims, 6 Drawing Sheets

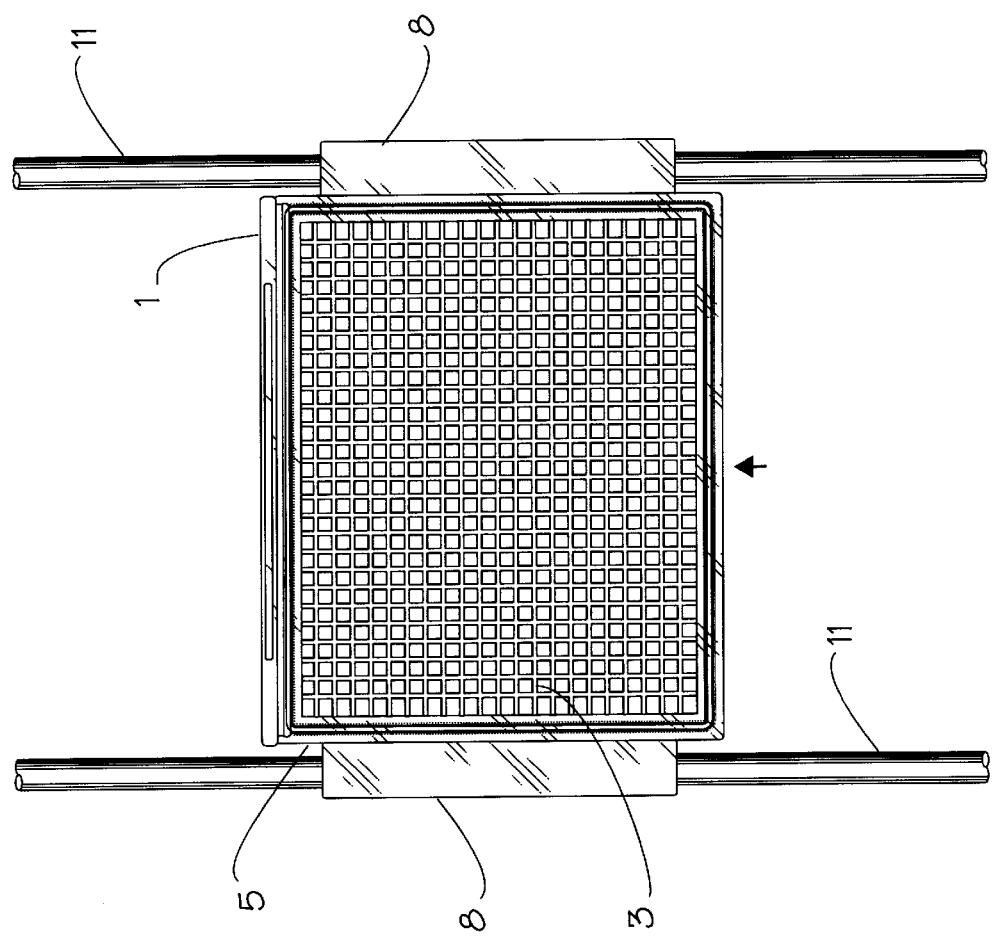

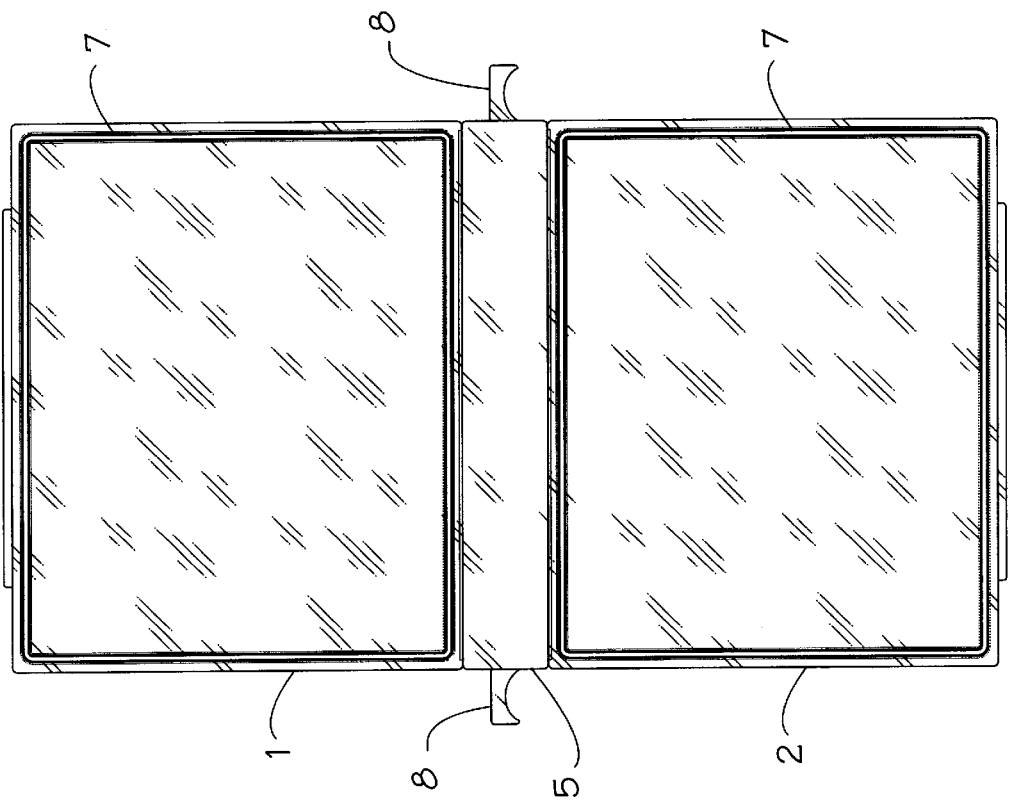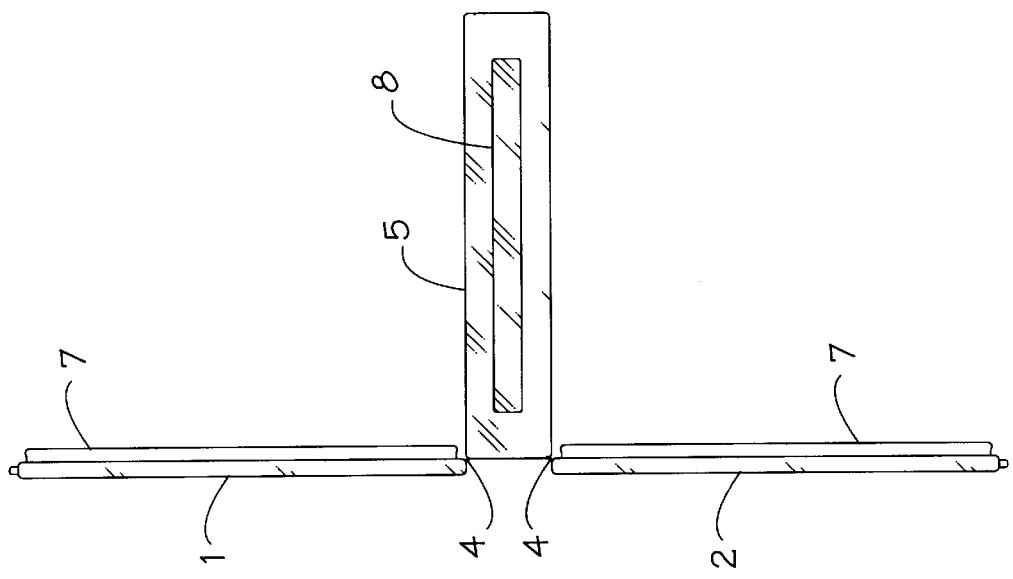

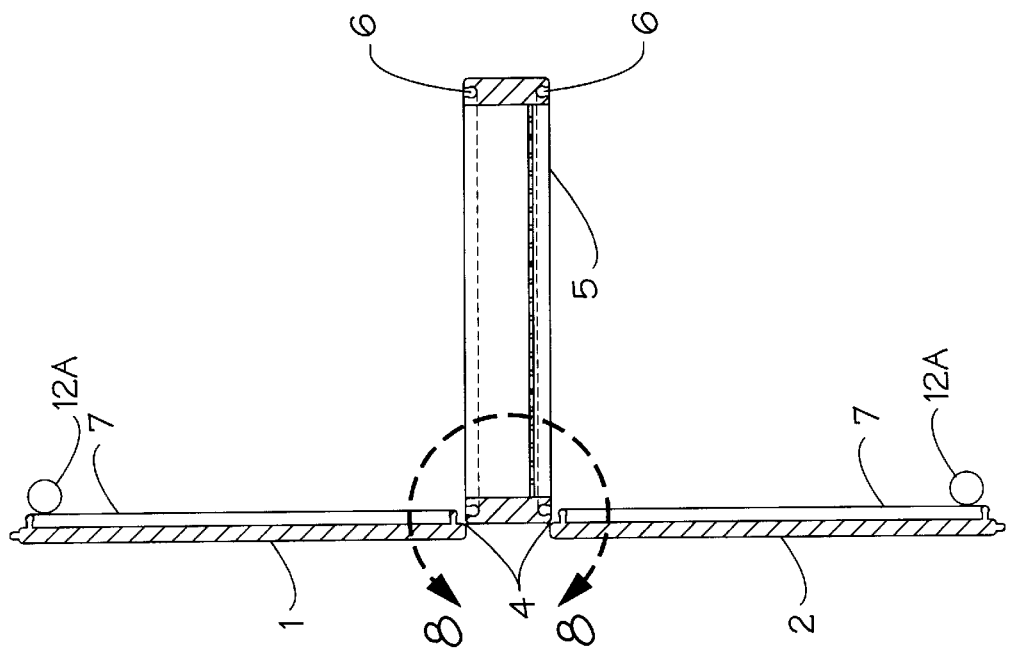
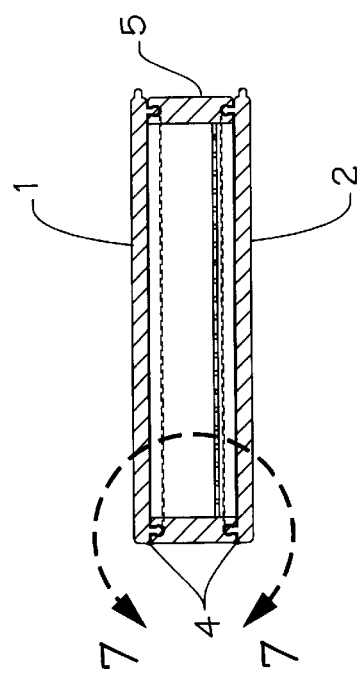

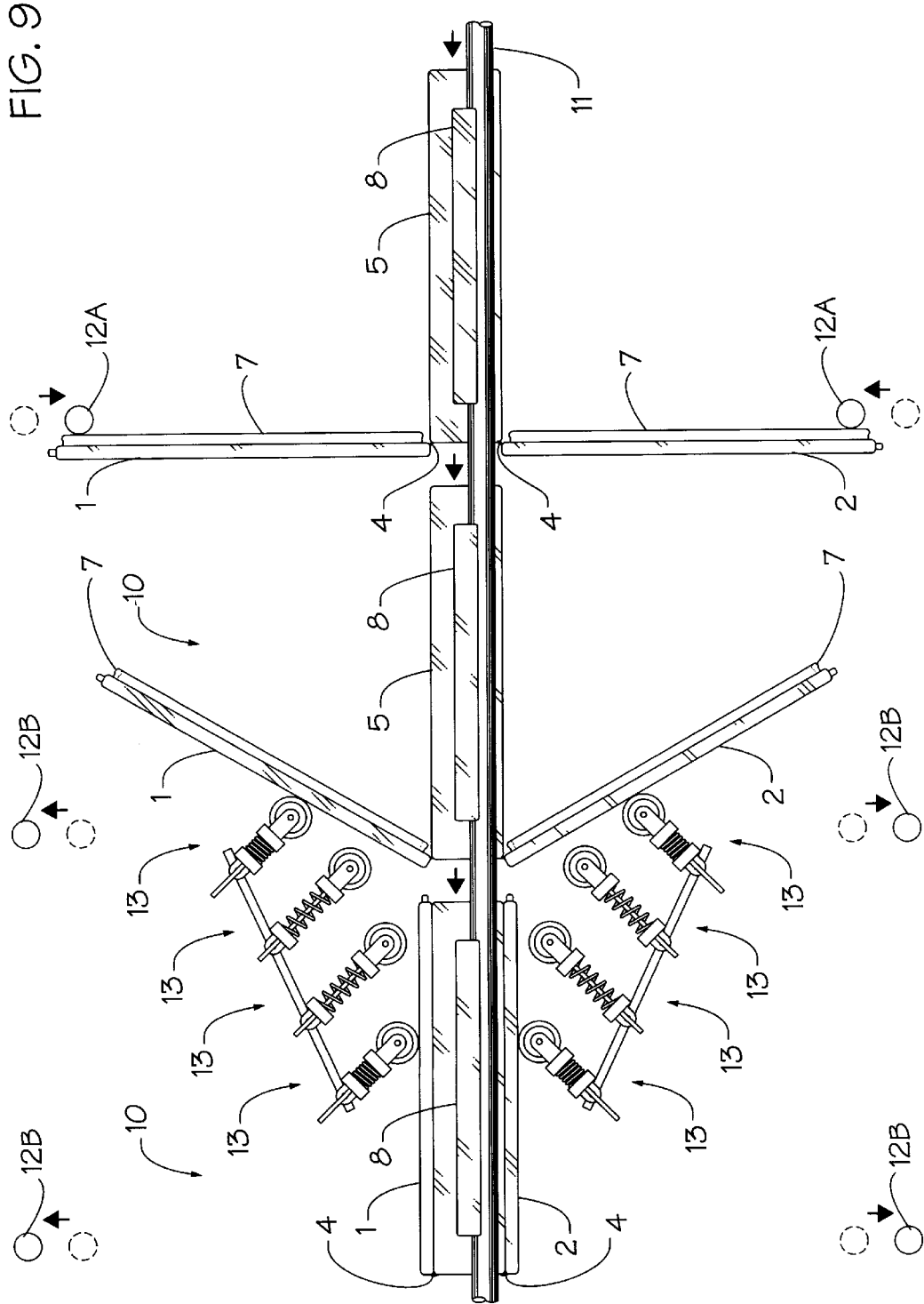

CONTAINER AND DEVICES TO ASSURE STERILIZATION OF SURFACES AND DEVICES BY ELECTRIC FIELD AND STERILIZING MEDIA

BACKGROUND

1. Field of Invention

This invention relates generally to systems, devices and methods for containing instruments and other similar devices during low temperature sterilization processes employing an electric field and, following sterilization, sealing the sterilized instruments and devices in said container.

2. Description of Prior Art

This invention relates generally to systems, devices and methods for containing instruments and other similar medical devices during low temperature sterilization processes utilizing an electric field such as those described in U.S. Pat. No. 4,643,876, U.S. Pat. No. 4,756,882 and U.S. Pat. No. 5,750,072.

Recent practices and regulations define the requirement for packaging methods and means to assure the preservation of the sterilized condition of medical devices and objects which have been sterilized by low temperature non radiation means. These requirements are presently accomplished by several steps or procedures;

First, the medical device(s) or object(s) to be sterilized are inserted in a package or enclosure fabricated of a material or means which will permit transfer of sterilant. The package completely surrounds the device(s)

Next, the opening of the package or enclosure is completely sealed,

Then, the device(s) or object(s) in their sealed package are placed in a sealed sterilizer compartment, Where, a vacuum is created, While a sterilant in plasma or vapor form is introduced into the chamber, With the sterilant penetrating the package due to the pressure differential between the chamber and the package, Following which the vacuum is released, Which is followed by the creation of a new vacuum And sterilant plasma or vapor is again introduced into the chamber. To assure effective exposure of the sterilant to all surfaces of the packaged medical devices and objects these processes normally require a sequence of infusions and subsequent evacuations of the sterilant to and from the permeable package.

These processes and sequences require significant time to complete sterilization. In part due to the restrictions on exposure of the sterilant to the devices and objects imposed by the packaging barrier. Certain of these systems produce potentially harmful vapors or chemical residuals which require evacuation procedures and substantial additional time to dissipate.

Our invention positions a specially designed open container holding the medical devices and objects to be sterilized within the cabinet of a low temperature electric field sterilizing system as taught by U.S. Pat. No. 4,643,876, U.S. Pat. No. 4,756,882 and U.S. Pat. No. 5,750,072. The container is open at the top with an open grid bottom to assure complete exposure of the medical devices and objects to the sterilant introduced into the sterilizing cabinet or processing section of a continuous process system.

This method allows shortening the exposure time required to provide sterilization as the medical devices and objects are directly exposed to the sterilant.

Following completion of the sterilization cycle, sterile desiccated air is introduced into the sterilizer cabinet or processing section to remove any residual moisture from the medical devices and objects.

Following moisture purging, the containers are moved through a series of rollers, which slowly closes the top and bottom lids of the container. The pressure from these rollers ensures that the plastic male ridge in each lid engages the female ridged groove in the body of the container, thereby sealing the top and bottom lids. The type of plastic from which the containers are formed permit momentary transitional distortion without any residual memory or effect of the distortion being retained. Clearances designed into the retainer groove and ridged rims on the lids anticipate momentary distension of the plastic to create a pressure fit.

To further assure a complete seal between the rim appendage and the retainer groove of the closure, a sealant containment strip may be inserted in the groove of the top and bottom closures. Mechanical pressure asserted on the top and bottom closures fractures capsules of the sealant containment strip releasing the sealant.

Dependent on the type of plastic and construction of the container these capsules may contain chemicals which polymerize the plastic of the retainer groove to effect an integral bond between the closure and body of the container. Alternatively, the sealant capsules may contain a pliant material which, when released by pressure fracture, surrounds the ridge of the container side sealing the closure to the body of the container.

In the batch processing configuration of our system when all of the containers have been sealed, the sterilization chamber is opened and the carriers holding the containers are moved to a location where the sterilized containers are removed from the carrier, labeled and placed in inventory. Alternatively, in the continuous production line processing configuration of our system the containers are moved along a conveyor system through the sterilizing field, drying section, the closure system and finally, to an inventory holding area.

Due to the normal temperature differential found in most environments using medical instruments and devices relative to that of the sterilization system enclosure, the now sealed containers will develop a nominal vacuum.

The containers are designed to be injection molded from a clear plastic material to assure direct visual confirmation of the contents of each container.

In sterile environments as in an operating room, containers without top or bottom lids may be utilized eliminating the requirement for sealing the container lids.

In certain sterilization systems as in U.S. Pat No. 5,750,072, sterilization may be effected in less than a minute. Such a system utilizing the container and methods described herein permit a significant reduction in the time required to sterilize instruments and devices thereby reducing sterilization costs while improving instrument and device utilization.

OBJECTS AND ADVANTAGES

Accordingly, several objects and advantages of our invention are;

Use of an open container to hold medical devices and objects during a low temperature sterilization process. The open container assures direct and maximum exposure of the contained devices and objects to the sterilant. This direct method eliminates the extended cycles and time required by other systems to assure sterilant penetration of a sealed closed packaging barrier.

Following completion of the sterilization cycle, evacuation of moisture from the open containers is accomplished by a blower system followed by closure of the container. Thereby assuring complete desiccation of the devices and objects. This method reduces the extended time required by other systems which evacuate sterilant residuals and by-products through sealed, closed instrument packaging A method and means to assure an integral bond and complete seal between the container and its closures. Thereby assuring complete and impervious containment of the sterilized medical instruments and devices. Other processes utilize sealed closed instrument and device packaging through which sterilant and its by products are inserted and removed. The processed instruments in the same sealed packaging are inventoried prior to use. The potential for penetration of contaminants is apparent.

A means and method for sealing the container immediately following completion of sterilization while it remains in the sterilized field.

Still further objects and advantages will become apparent from a consideration of the ensuing description and accompanying drawings.

BRIEF DESCRIPTION OF THE DRAWINGS

FIG. 2 is a plan view with the lids open showing the bottom grid and the side handles which position the container as it moves through the process.

FIG. 3 is a side elevation with the lids open.

FIG. 4 is a front elevation showing the container with top and bottom lids open. The sealing ridges are shown in position in the perimeter of the lids.

FIG. 5 is a side section showing the lids closed with the sealing ridges in place in the female grooves of the body.

FIG. 6 is a side section with both lids open.

FIG. 9 shows three stages of the mechanical action to close and seal the lids to the body following processing. The container is shown at the right following sterilization and drying processing with lids held in open by a retaining arm. The container is held in place by the side handles as it is moved forward. The next position shows the retaining arms withdrawn from the lids permitting them to begin to close. The last position shows the lids mechanically closed by action of spring loaded rollers.

REFERENCE NUMERALS FOR DRAWINGS

Figure 1:
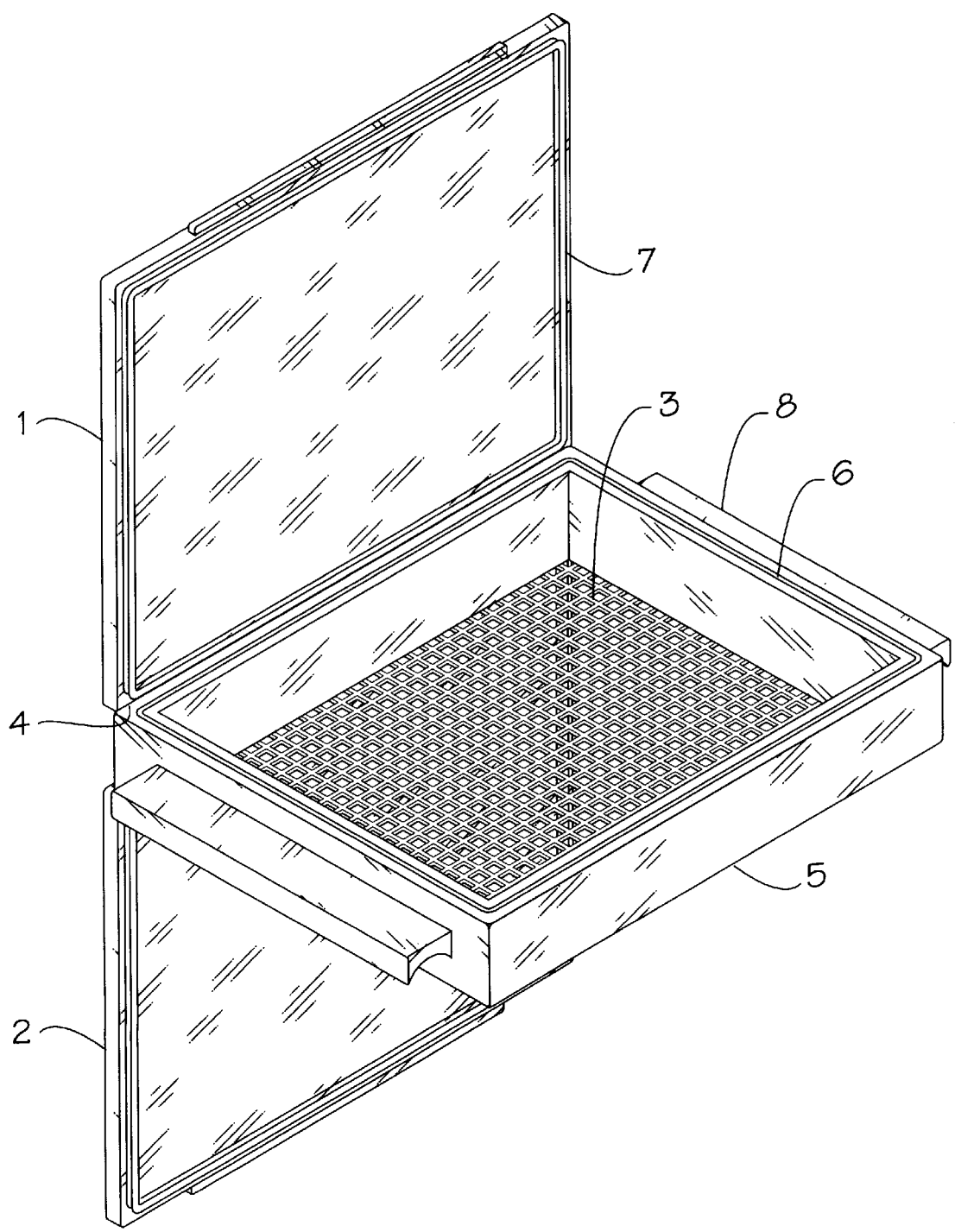
FIG. 1 is a three dimensional view showing the container, top and bottom lids and the open grid bottom.

FIG. 1
1 Clear plastic top lid
2 Clear plastic bottom lid
3 Open plastic bottom grid of the container body.
4 Molded flexible hinge
5 Container body of clear plastic
6 Female body groove to accept sealing ridge of the top
7 Male ridge of the top which is inserted into body groove.
8 Container handles.

FIG. 2
1 Clear plastic top lid
3 Open plastic bottom grid of the container body.
5 Container body of clear plastic
8 Container handles
11 Support rails of the processing system.

FIG. 3
1 Clear plastic top lid
2 Clear plastic bottom lid
4 Molded flexible hinge
5 Container body of clear plastic
7 Male ridge of the top which is inserted into body groove.
8 Container handles.

FIG. 4
1 Clear plastic top lid
2 Clear plastic bottom lid
4 Molded flexible hinge
5 Container body of clear plastic
7 Male ridges of the top and bottom lids which are inserted into body grooves
8 Container handles.

FIG. 5
1 Clear plastic top lid
2 Clear plastic bottom lid
4 Molded flexible hinge
5 Container body of clear plastic FIG. 6
1 Clear plastic top lid
2 Clear plastic bottom lid
4 Molded flexible hinge
5 Container body of clear plastic
6 Female body groove to accept sealing ridge of the top
7 Male ridges of the top and bottom lids which are inserted into body grooves
12A Processing system lid retainer.

Figure 7:
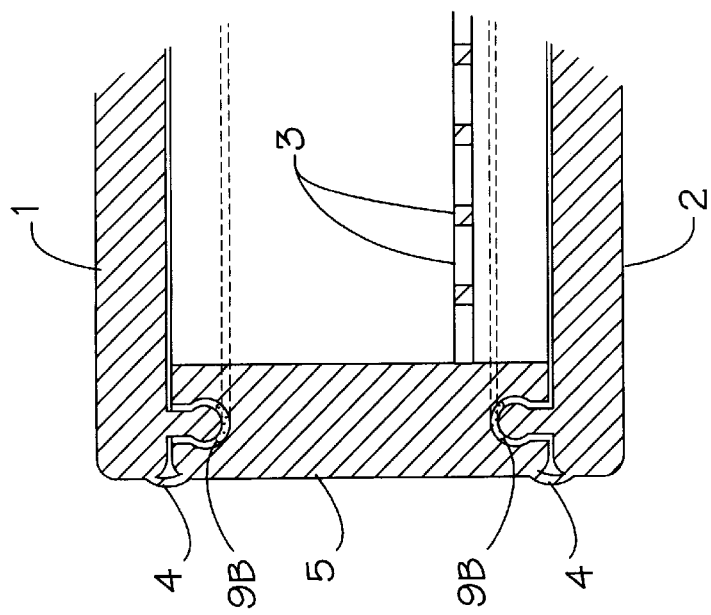
FIG. 7 is a side section of the container as identified in FIG. 5. It shows the lids closed and details the fit of the sealing ridges in the body grooves.

FIG. 7
1 Clear plastic top lid
2 Clear plastic bottom lid
3 Open plastic bottom grid of the container body
4 Molded flexible hinge
5 Container body of clear plastic
9B Cavity clearance between male ridges of top and bottom and body grooves.

Figure 8:
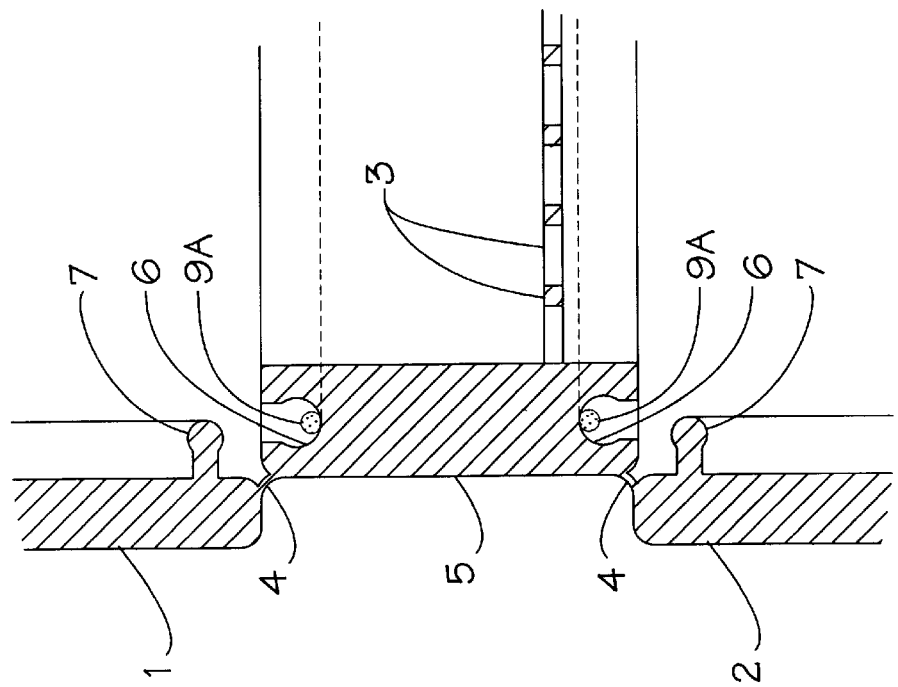
FIG. 8 is a side section of the container as identified in FIG. 6. It shows the lids open and sealant material in place in the top and bottom female grooves of the body.

FIG. 8
1 Clear plastic top lid
2 Clear plastic bottom lid
3 Open plastic bottom grid of the container body
4 Molded flexible hinge
5 Container body of clear plastic
6 Female body grooves to accept sealing ridges of the top and bottom.
7 Male ridges of the top and bottom lids which are inserted into body grooves
9A Sealant material FIG. 9
1 Clear plastic top lid
2 Clear plastic bottom lid
4 Molded flexible hinge
5 Container body of clear plastic
6 Female body grooves to accept sealing ridges of the top and bottom.
7 Male ridges of the top and bottom lids which are inserted into body grooves.
8 Container handles
11 Support rails of the processing system.

12A Processing system lid retainer in retaining position
12B Processing system lid retainer in retracted position
13 Spring loaded lid closing rollers of the processing system.

PREFERRED EMBODIMENT—DESCRIPTION

The preferred embodiment of the sterilizing system container is as shown in FIG. 1, a clear plastic container body (5), with molded flexible hinges (4) attaching a top lid (1) and a bottom lid (2) to the main body of the container. A molded open grid structure (3) forms the bottom of the body of the container. It supports and retains the devices to be sterilized while permitting the free flow of sterilant around those devices. When sterilization is completed, the container is closed with a female groove (6) in the top and bottom of the side of the body of the container expanding sufficiently to accept the ridges of the top and bottom (7). This action alone provides a seal of substantial integrity. To assure a seal of greater integrity, the female groove may contain sealing materials, shown as 9A in FIG. 8. These sealant materials may be a neoprene flexible strip, or in different embodiments, sealing polymers encapsulated in a strip. These polymers are released and activated when pressure is applied by the male ridges of the top and bottom to the sealant strip fracturing the containing membrane of the strip. The container body is molded with handles at its sides. These handles act to guide and orient the container during sterilization processing. Following processing they provide a convenient means for transporting and inventorying the containers.

PREFERRED EMBODIMENT—OPERATION

Medical devices and objects to be sterilized are placed in an open container. Filled containers are then placed in position and retained on the sterilizer carrier system by engagement with handles at the sides of the containers. In a separate operation sealant strips containing encapsulated sealants may have been inserted in the annular retainer groove strips of the top and bottom closures. The top and bottom lids are retracted and held in an open position by retainer rods integrated with the processing carrier mechanism In the batch processing system, the sterilizer enclosure is closed and secured and the sequence of sterilizing operations is initiated. At the conclusion of the sterilizing operations, sterile desiccated air is introduced into the sterilizer cabinet to remove any residual moisture from the medical devices and objects contained within the containers.

Following completion of the drying operation, as shown in FIG. 9, the containers are moved to engage rollers (13). The rollers (13) have a spring loaded resistance which exerts pressure on the lids as they are advanced into the rollers. FIG. 9 shows the lids closing as the container is pushed further into the rollers.

While the invention has been described with reference to one preferred embodiment, it is to be clearly understood by those skilled in the art that the invention is not limited thereto. Rather, the scope of the invention is to be interpreted only in conjunction with the appended claims.

CONCLUSIONS, RAMIFICATIONS AND SCOPE

Accordingly, it can be seen that the invention substantially reduces the time required to complete sterilization as compared to other sterilization methods. Further, the method of the invention produces a secure containment of the sterilized medical devices and objects.

Although the description above contains many specifications, these should not be construed as limiting the scope of the invention but as merely providing illustrations of some of the presently preferred embodiments of this invention. Various other embodiments and ramifications are possible within it's scope.

Thus the scope of the invention should be determined by the appended claims and their legal equivalents, rather than by the examples given.

SUMMARY

The principal objective of this invention is to provide a container which substantially reduces the time required to effect sterilization of contained objects and operates in conjunction with a sterilization method which is effective without using high temperature, toxic chemicals, harmful radiation or high electromagnetic energy levels.

What is claimed is:

1. A container for use in an automated sterilization system, comprising:

a container body having four upstanding sidewalls with a female groove around both an upper and lower surface thereof, an open grid bottom, and two closures, wherein a sealing member is contained within each of said female grooves;

said two closures including a first top closure and a second bottom closure, both said closures including a ridge around the face thereof, said top closure being attached to one of said four upstanding sidewalls by an integrally molded hinge at an upper surface of the sidewall and said bottom closure being attached to said same sidewall by an integrally molded hinge at a bottom surface of the sidewall, wherein said top closure is operable to matingly seal with the upper surface of the container body and said bottom closure is operable to matingly seal with the bottom surface of the container body; and two handles, each molded to an opposite sidewall of the container body.

2. A method for sterilizing objects, comprising:

(a) providing a container system wherein the container system comprises a container body having four upstanding sidewalls with a female groove around both an upper and lower surface thereof, an open grid bottom, and two closures, wherein a sealing member is contained within each of said female grooves;

said two closures including a first top closure and a second bottom closure, both said closures including a ridge around the face thereof, said top closure being attached to one of said four upstanding sidewalls by an integrally molded hinge at an upper surface of the sidewall and said bottom closure being attached to said same sidewall by an integrally molded hinge at a bottom surface of the sidewall; and two handles, each molded to an opposite sidewall of the container body;

(b) opening the container and placing the object to be sterilized into the container;

(c) exposing the object simultaneously to a sterilizing fluid mist and an electric field, whereby said fluid mist is maintained in a free radical state by the electric field and said free radicals sterilize said objects;

(d) flowing sterile air past the container so as to remove remaining sterilant from the object; and (e) closing said two closures so as to seal the container body.

* * * * *